(12) United States Patent
Risch et al.

(10) Patent No.: US 11,730,617 B2
(45) Date of Patent: Aug. 22, 2023

(54) BALLOON CATHETER STENT DEVICE WITH STENT PROTRUSIONS

(71) Applicant: BIOTRONIK AG, Buelach (CH)

(72) Inventors: Fabian Risch, Doerflingen (CH); Tobias Schäfer, Blumberg-Fuetzen (DE)

(73) Assignee: BIOTRONIK AG, Buelach (CH)

( * ) Notice: Subject to any disclaimer, the term of this patent is extended or adjusted under 35 U.S.C. 154(b) by 485 days.

(21) Appl. No.: 16/649,924

(22) PCT Filed: Sep. 17, 2018

(86) PCT No.: PCT/EP2018/075041
§ 371 (c)(1),
(2) Date: Mar. 23, 2020

(87) PCT Pub. No.: WO2019/076557
PCT Pub. Date: Apr. 25, 2019

(65) Prior Publication Data
US 2020/0276039 A1    Sep. 3, 2020

(30) Foreign Application Priority Data
Oct. 18, 2017 (EP) .................................... 17196977

(51) Int. Cl.
*A61F 2/958* (2013.01)
*A61B 17/22* (2006.01)
*A61B 17/3207* (2006.01)
*A61F 2/844* (2013.01)

(52) U.S. Cl.
CPC .............. *A61F 2/958* (2013.01); *A61B 17/22* (2013.01); *A61B 17/320725* (2013.01); *A61F 2/844* (2013.01); *A61B 2017/22051* (2013.01); *A61F 2230/0089* (2013.01)

(58) Field of Classification Search
CPC .. A61F 2/958; A61F 2/844; A61F 2230/0089; A61B 17/22; A61B 17/320725; A61B 2017/22051; A61B 2017/22001
See application file for complete search history.

(56) References Cited

U.S. PATENT DOCUMENTS 5,397,355 A * 3/1995 Marin ....................... A61F 2/91
                                                        623/1.2
5,634,928 A * 6/1997 Fischell .................. A61F 2/958
                                                        623/1.11

(Continued)

OTHER PUBLICATIONS

Neumann, Elisabeth, International Search Report for Application No. PCT/EP2018/075041, dated Jul. 12, 2018.

(Continued)

*Primary Examiner* — Tan-Uyen T Ho
*Assistant Examiner* — Chima U Igboko
(74) *Attorney, Agent, or Firm* — Greer, Burns & Crain, Ltd.; Steven P. Fallon

(57) ABSTRACT

A balloon catheter-stent device includes a balloon catheter has a catheter tube and a radially expandable balloon. A stent surrounds the balloon. The stent can be radially expanded in its radial extent by the balloon. The stent includes at least one folding protrusion, which unfolds with radial expansion and axial shortening of the stent to form an outer stent protrusion.

18 Claims, 5 Drawing Sheets

(56) References Cited

U.S. PATENT DOCUMENTS

| | | | |
|---|---|---|---|
| 5,681,346 A * | 10/1997 | Orth | A61F 2/915 606/198 |
| 5,855,597 A | 1/1999 | Jayaraman | |
| 2002/0010489 A1 | 1/2002 | Grayzel et al. | |
| 2003/0220683 A1 | 11/2003 | Minasian | |
| 2014/0277562 A1 | 9/2014 | Seddon et al. | |
| 2015/0216552 A1 * | 8/2015 | Hefer | A61M 25/104 606/159 |

OTHER PUBLICATIONS

Neumann, Elisabeth, European Search Report for Application No. 17196977.7 dated Apr. 25, 2018.

* cited by examiner

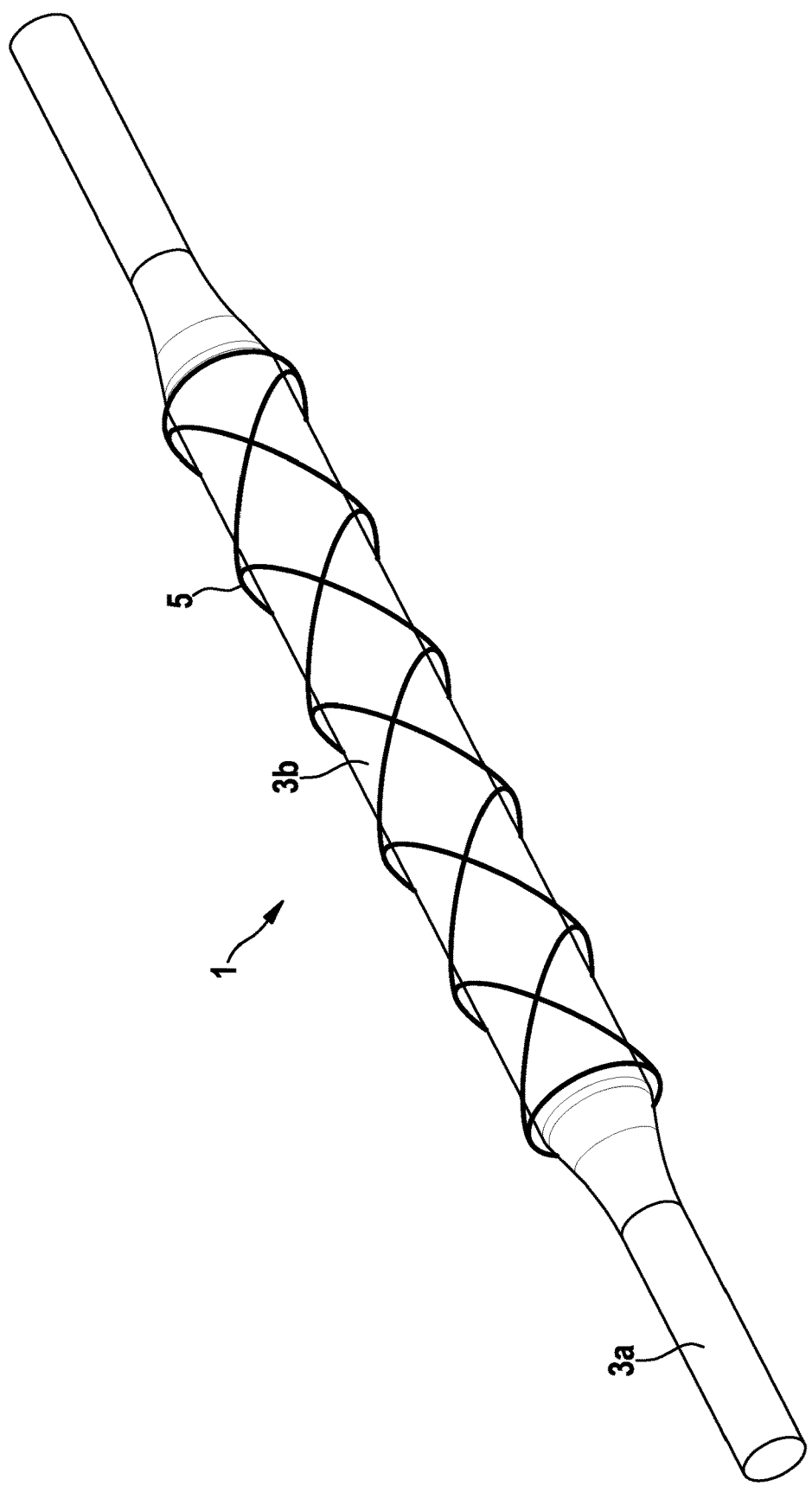

BALLOON CATHETER STENT DEVICE WITH STENT PROTRUSIONS

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2018/075041, which was filed Sep. 17, 2018, which application claimed priority from European Application EP17196977.7, which was filed Oct. 18, 2017.

FIELD OF THE INVENTION

The invention relates to a stent for a balloon catheter-stent device which includes a balloon catheter and a stent surrounding the balloon.

BACKGROUND

Balloon catheter-stent devices are used in a clinical setting for the treatment of vasoconstrictions (stenoses) of blood vessels. Expansion (dilatation) of a balloon catheter is supplemented by a stabilisation of the expanded vessel portion with the stent that is expanded by the balloon and left behind at the location of the stenosis following the deflation of the balloon and the withdrawal of the balloon catheter (stenting). Reference is made, purely by way of example, to DE 10 2004 059 523 A1 in respect of devices of this kind, which describes a new stage of development of these devices.

Often, at least partial removal of deposits on the vessel wall is desirable in addition to the expansion and stabilisation of the stenosis portion. For this purpose, balloon catheters having what are known as cutting balloons with cutting blades on the balloon surface and more recently also stents having scoring elements for cutting vascular deposits have been developed and are also used already in a clinical setting.

Document WO 2009/046206 A1 presents a balloon catheter with attached scoring elements. The scoring elements are helically extending metal wires or comparable plastic elements attached to the balloon of the balloon catheter. Document U.S. Pat. No. 8,348,987 B2 presents a balloon catheter-stent device with scoring elements attached to the stent structure.

It has been found that both solutions have significant disadvantages.

Cutting balloons are relatively rigid on account of the attached cutting elements and can only be introduced with difficulty into complex lesions, and there is a significant risk of perforation here as well. In addition, the minimum (deflated) balloon diameter is larger than in comparable balloons without cutting elements. Lastly, cutting balloons put up a relatively high resistance as the device is advanced through the vessel system, which hinders precise handling.

In stents with scoring elements there is the risk, inter alia, that the scoring elements, which also protrude in the insertion state, might cause tissue damage. On the other hand, the effects actually attained at the intended site of insertion have not proven to be satisfactory in clinical studies.

SUMMARY OF THE INVENTION

A balloon catheter-stent device includes a balloon catheter having a catheter tube and a radially expandable balloon. A stent surrounds the balloon and is radially expandable by inflation of the balloon. The stent includes at least one folding protrusion that unfolds with radial expansion and axial shortening of the stent to form an outer stent protrusion.

A stent includes a regular lattice structure formed of lattice bar elements and at least one folding protrusion arranged within the lattice structure that unfolds with radial expansion and axial shortening of the stent to form an outer stent protrusion, wherein the at least one folding protrusion has a folded position with respect a global peripheral surface of the stent when folded and extends a height beyond the folded position when unfolded.

BRIEF DESCRIPTION OF THE DRAWINGS

Advantages and expedient features of the invention will also become clear from the following description of an exemplary embodiment with reference to the drawings, in which:

FIGS. 1A and 1B show sketched perspective views of the basic structure of a balloon catheter-stent device in the starting state and in the dilated end state, respectively.

DETAILED DESCRIPTION OF THE PREFERRED EMBODIMENTS

Figure 1B:
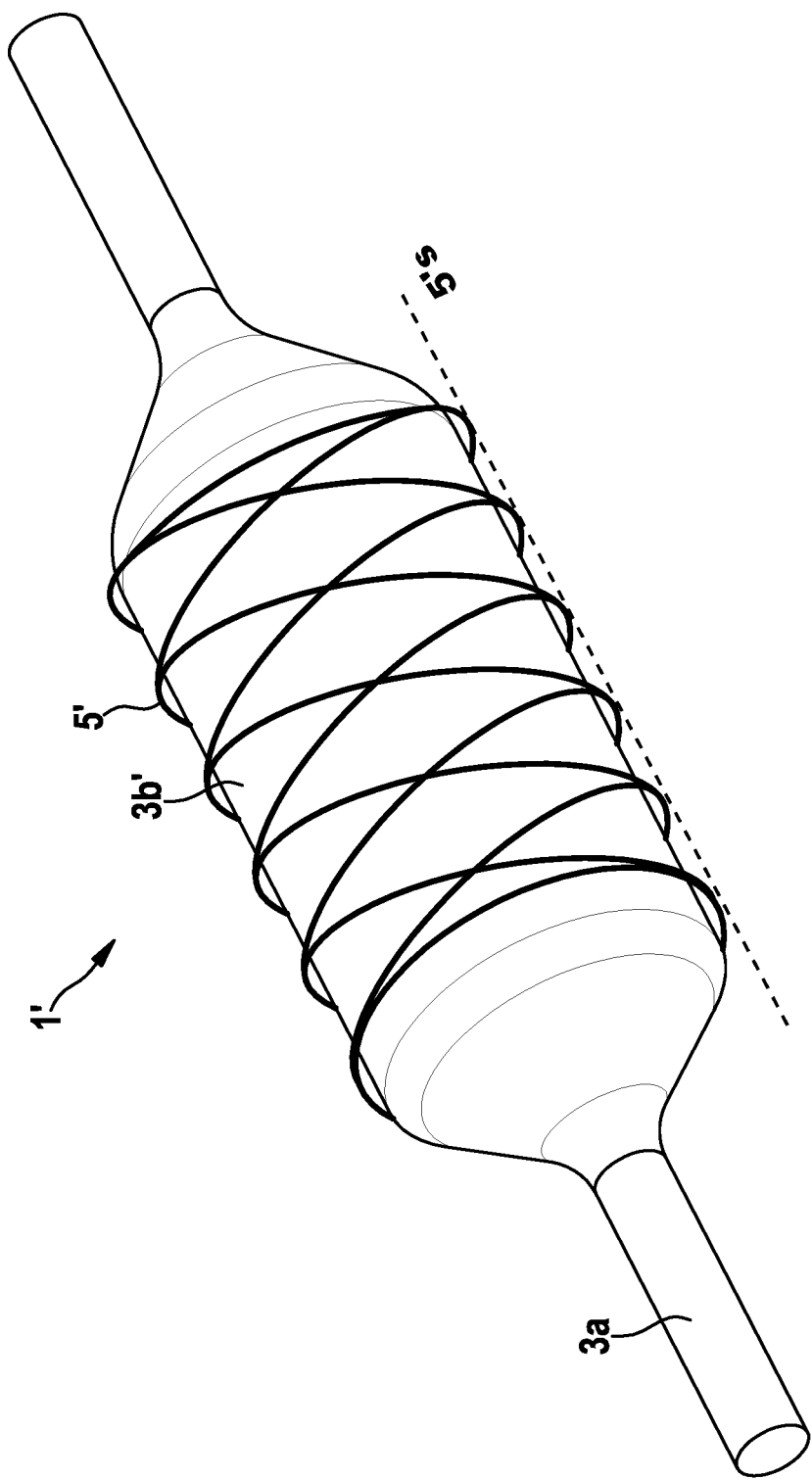

The provides a balloon catheter-stent device with at least one protrusion element, preferably a plurality of elements, incorporated in the surface of the stent in the starting state (non-expanded state), but protruding locally from the surface of the stent in the state of use or end state (dilated state of the stent) and hereby can attain a working effect relative to material layers surrounding the stent in the state of use. These stent protrusions unfold with the deformation experienced by the stent at the time of the dilatation.

Axial shortening of the stent, which is experienced necessarily in the case of a balloon catheter-stent device with the radial expansion by the inflation of the balloon, aids erection of the folding protrusion. Radially expandable stents have a meandering or zig-zagging or other wave structure in the peripheral direction. Upon radial expansion, these structures are drawn away from one another in the peripheral direction and at the same time are compressed accordingly in the axial direction. Put more simply, the wavelength of a structure running in the peripheral direction becomes greater, whereas its amplitude is reduced. The forces acting in a shortening manner in the axial direction are utilised in the present invention to unfold and erect the stent protrusions.

At least in preferred embodiments, the following advantages inter alia are achieved with the solution according to the invention:

A large radial expansion is achieved by the folding protrusion. This allows a very small cross-section of the balloon catheter. Thus, stenoses can be reached which otherwise could not be expanded or could be expanded only with a multi-step procedure.

The erection of the stent protrusions is guided by the folding protrusion, and the structure and is robust.

Flexible designs are possible depending on the application (breaking-up of stenoses or anchoring for example of heart valves).

Advantageous transport and feeding of the implant on account of a small cross-section and relatively undisturbed surface.

In principle, the present solution and the attainment of the aforesaid advantages also can be achieved in a pure stent device (without balloon catheter). Then, the same stent structure is dilated not by the balloon of the balloon catheter, but in another way, and the dilatation realises the same functions and has the same effects as described above. However, the device with balloon catheter is currently preferred, because it can provide greater tangential or radial forces and should thus enable a fundamentally more robust and reliable embodiment of the invention. Furthermore, the balloon catheter-stent device is configured such that the stent is fixedly connected to the balloon catheter. It is thus ensured that the stent together with the balloon catheter is removed again from the body of the patient following the dilatation.

In embodiments of the invention the folding protrusions are designed in such a way that, as they are unfolded and erected, they form outer stent protrusions of a height above the global end peripheral surface of the stent, this being dependent on the global end periphery of the stent in question. This enables, to a certain extent, an "automatic" adjustment of the effective height of the tool portions (or anchoring aids) created with the stent protrusions to the dimensions of the vessel to be treated or of the lesion in question.

In preferred embodiments of the invention the folding protrusions are designed in such a way that, as they are unfolded and erected to an increasing extent, an axial and a radial and/or tangential movement component occurs. As a result, a relative movement in relation to the surrounding stenosis and therefore a certain working effect can be attained already during the process of inflation of the balloon and dilatation of the stent, without the need for any special movement here of the balloon catheter.

In a further embodiment of the invention the folding protrusions are designed in such a way that in the starting state of the stent they lie in a manner folded flat over the global starting peripheral surface of said stent or are not raised therefrom by more than 20%, preferably not more than 1% to 10%, of the starting radius. In respect of the simplest possible and safe insertion of the device, this enables a desirable "undisturbed" surface contour of the undilated stent. The folding protrusion in the starting state of the stent (and also in the crimped state during implantation) preferably lie in the starting peripheral surface, i.e. the folding protrusions do not extend radially beyond the rest of the strut structure of the stent. Folding protrusions that are raised beyond the starting peripheral surface are used expediently only in special cases. In these special cases, the folding protrusions are advantageously raised beyond the starting peripheral surface by no more than 20%, preferably between 1% and 10%, of the starting radius.

The combination of the balloon and stent located thereon with folding protrusion is expediently compressed to an outer diameter between 1.2 mm and 2.2 mm, such that the combination is suitable for insertion into the body of the patient via a 4F to 6F access point. The balloon and thus the inner diameter of the stent with folding protrusions can advantageously be expanded to a diameter between 2 mm and 10 mm. The folding protrusions ensure a radius enlargement of up to 1.7 mm. Depending on the ratio between compressed and expanded diameter of the stent, the stent is shortened by up to 15 mm during the expansion. The folding protrusions preferably ensure a diameter enlargement in the expanded state to a value between 110% and 200%, preferably between 125% and 175%, particularly preferably between 130% and 160%. Here, 100% corresponds to the diameter of the expanded stent without folding protrusions.

The axial shortening, as already explained, drives the radial erection of the folding protrusions. In an advantageous embodiment of the invention the axial shortening can be utilised for an additional relative movement of the folding protrusions relative to the vessel wall. In this embodiment the stent design is selected such that an extreme axial shortening by practically 100% of the stent length accompanies the expansion. In a preferred embodiment the stent design is selected such that, in the event that the stent diameter is doubled proceeding from the maximally compressed state, the stent length decreases by at least 20%, preferably by at least 50%, more preferably by at least 70%, even more preferably by at least 90%, and most preferably by at least 100%. A maximally compressed diameter is understood to mean the diameter of a stent at which the stent is compressed to such an extent that the stent struts forming the periphery of the stent are pressed against one another such that a further axial compression can be achieved only with deformation of the stent or bends or breaks in the stent structure. As a result of the shortening of the stent during expansion, the folding protrusions are not only erected, but also change their axial position relative to the catheter, i.e. the folding protrusions move distally or proximally in respect of the catheter axis and therefore also in respect of the vessel wall to be treated. In this embodiment the stenosis can thus be actively broken up, similarly to being cut off. As a result of this operating principle, the folding protrusions are provided with a cutting or abrading function, and in particular with no anchoring function.

In further embodiments of the invention the folding protrusions in the folded and erected state have a substantially pyramid shape or superimposed tetrahedron shape. In principle, many other designs of the folding protrusions are possible, provided the structure thereof is not too complex and the targeted unfolding under use conditions is ensured in a reliable manner. The choice of a specific geometry is also dependent on the field of use and the primary intended function of the stent protrusions (for example forcing open or removal of stenoses or anchoring of the stent).

In further embodiments the stent has a regular lattice structure formed from lattice bar elements, and the folding protrusions are formed at least in part by lattice bar elements or are fixedly attached thereto. Stents which are formed from regular lattice structures are known and approved in a wide range of designs, and their production is technically developed and economical. The aforementioned embodiment of the invention can build on these advantages and can thus likewise lead to particularly reliable and economical products.

The folding protrusions are in particular configured such that they are attached to or provided on the surface of the stent in a planar manner and are preferably stretched between at least two stent struts or individual pieces of at least one stent strut having different directions. As a result of the dilatation of the stent, the stent struts or stent strut pieces experience a movement towards one another, whereby the folding protrusions attached or provided therebetween in a planar manner experiences a compression which causes said folding protrusions to unfold outwardly, i.e. in the radial direction, and, in the body of the patient, in the direction of the tissue.

In addition, the folding protrusions can be formed integrally with the rest of the structure of the stent and in particular by protrusions of the same shaping process, for example by substantially single-step laser cutting of the overall structure from a tubular semifinished product. Alternatively, the folding protrusions can be formed of a different material compared to the rest of the structure of the stent and can be attached thereto in a separate attachment step. The latter variants enable a particularly differentiated embodiment of the folding protrusions, with simultaneous use of an approved main stent structure.

In further embodiments it is provided that end portions or points of fold edges of the folding protrusions are formed with cross-sectional taperings or perforations as predetermined bending points or with a shape-memory material. The location where the folding protrusions are folded can thus be determined in advance by material weakenings or by impression of the shape (for example in the case of Nitinol). It is ensured by appropriate taperings and/or by the balloon arranged beneath the folding protrusion that the folding protrusion opens out outwardly.

In embodiments that are currently preferred and that are focused directly on the underlying problem, at least part of each of the folding protrusions has at least one cutting or sawing edge for engaging in an outer material in a cutting or sawing manner, in particular a stenosis of a blood vessel. The function of the tool formed by the one or more cutting or sawing edge(s) can vary within wide limits by the geometry of the underlying folding protrusions and the selective placement of the corresponding working edge(s).

In other embodiments at least part of each of the folding protrusions has at least one bent, in particular concavely curved fixing edge for engagement in an outer structure, in particular the wall of a blood vessel or organ.

In further embodiments elastically (or possibly also plastically) deformable compensation regions for reducing the resultant shortening of the stent are provided on the peripheral surface of the stent at least in intermediate regions between some folding protrusions. Depending on the arrangement, spring elements of this kind can also bring about a relative movement of the folding protrusions in relation to the stenosis which would be advantageous for the cutting of the calcification.

The folding protrusions can also be main elements, where other components are attached, for example a bar connected to a plurality of folding protrusions.

The stent structure can lie loosely on the balloon, can be fixedly connected thereto, or also can be fixedly/loosely connected to the balloon neck or tube.

In the case of an implant that is to be better anchored by the folding protrusion, a loose connection to the balloon/tube is expedient.

For the preferred application of breaking up a stenosis, in which the scoring elements have to be guided out again, an at least partially fixed connection to the balloon/tube is necessary.

As scoring device, it is advantageous if the stent structure is made of a shape-memory material (for example Nitinol), so that it retracts again to the original cross-section once the calcification has been broken up. The shape of the stent structure impressed in the shape-memory material is in this case the original shape, where the folding protrusions are not erected. The force for erecting the folding protrusions is provided in this case by the inflation of a balloon. When the balloon is deflated the stent structure returns automatically to the impressed shape. The folding protrusions thus fold down again.

Other materials, however, are also conceivable, particularly if the structure is used for anchoring. In this case it is not necessary for the folding protrusions to be folded back down. However, materials that have no shape-memory properties can also be considered for the stent and folding protrusions in the event that a stenosis is to be broken up. In this case, the materials are plastically deformed (the folding protrusions are erected) by the inflation of the balloon and are plastically deformed back again (the folding protrusions return to the compressed starting state) by the force of the deflating balloon. In this embodiment of the connection, the balloon and stent are fixedly connected, preferably over the entire bearing surface of the stent.

FIG. 1A schematically shows a balloon catheter-stent device 1, which includes a balloon catheter 3 with a catheter tube 3a and a balloon 3b and a stent 5 surrounding the balloon, in the non-inflated or undilated starting state, and FIG. 1B shows the dilated balloon catheter-stent device 1' with inflated balloon 3b' and stent 5' in an end state, as is brought about, following insertion into a vessel system, by inflation of the balloon for the purpose of treatment of a stenosis. The stent 5', as is known, has a lattice structure, which widens radially and shortens axially at the time of the dilatation.

Figure 2:
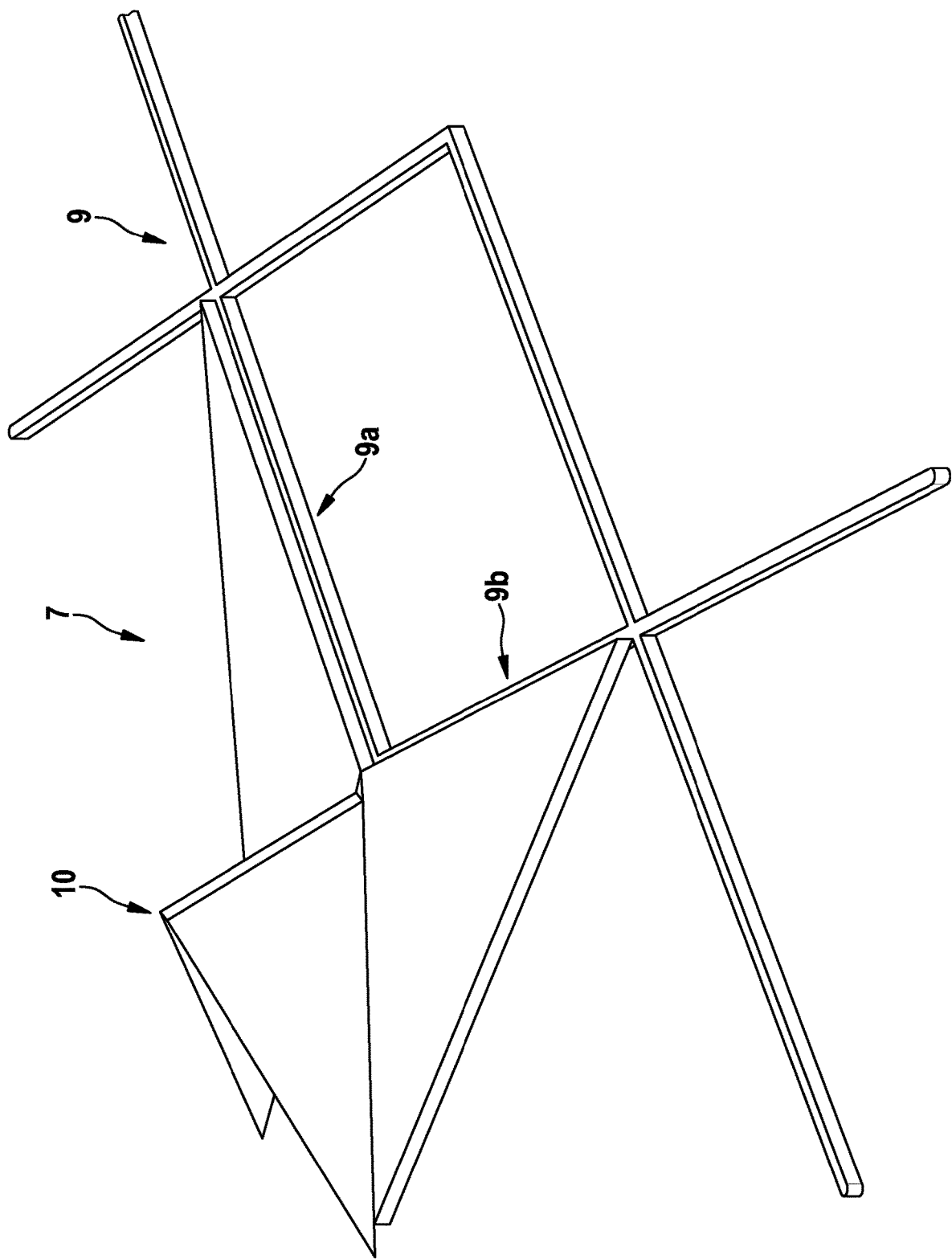
FIG. 2 shows a schematic view of the folding protrusion of an embodiment of the balloon catheter-stent device according to the invention.

FIG. 2 shows a schematic perspective view of a folding protrusion 7, in the form of a plate-like structure, which is attached to two adjacent lattice two bar elements 9a, 9b of a lattice structure 9 of a stent, in a folded end state, thus forming a protrusion 10 above the rest of the surface ("global peripheral surface 5's") of the stent. This state corresponds to the dilated state of the stent 5' shown in FIG. 1B, in which the lattice structure forming the peripheral surface is radially expanded, but axially shortened. The axial shortening causes the folding protrusion 7, which in the starting state lies substantially flat in the peripheral surface, to be unfolded and erected.

Figure 3:
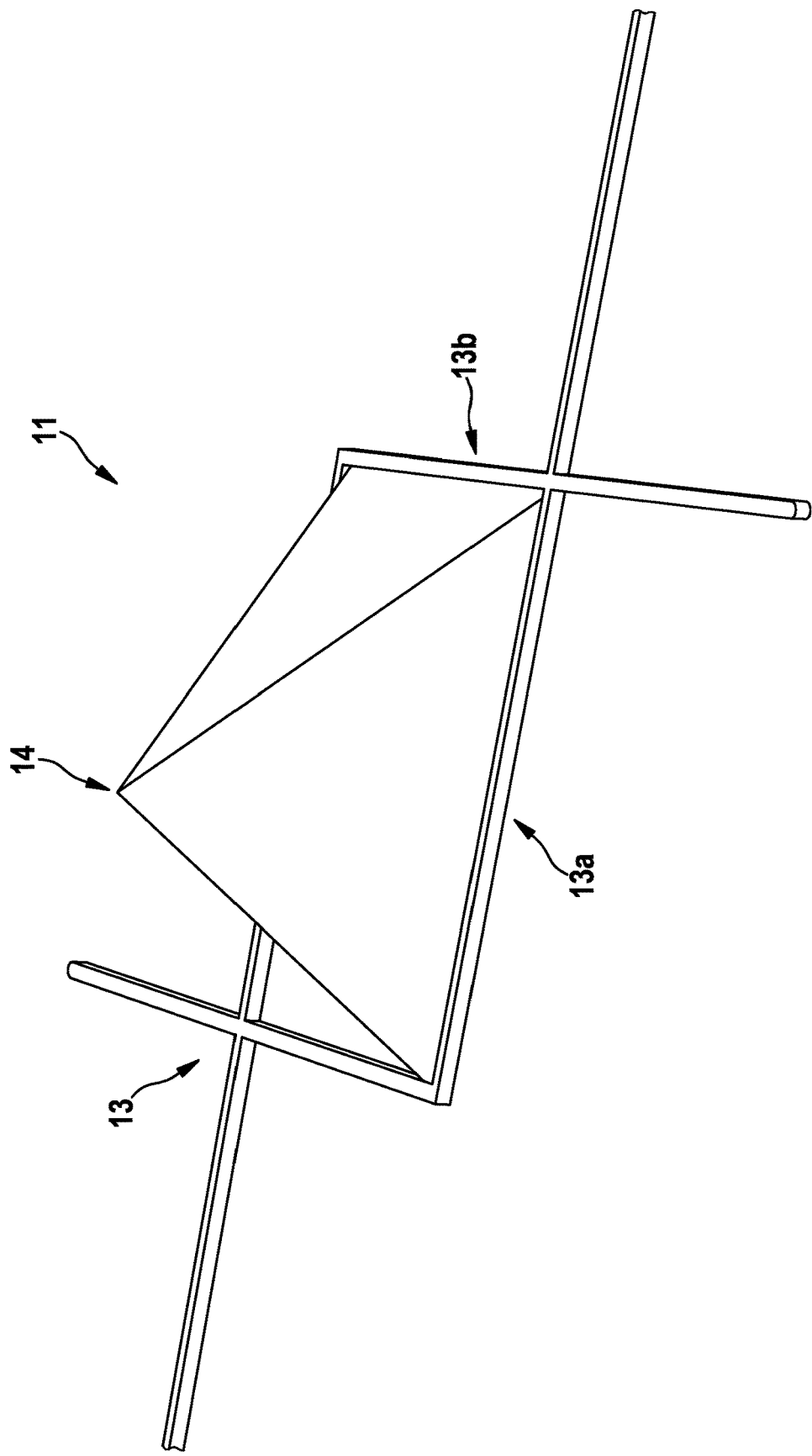
FIG. 3 shows a schematic view of the folding protrusion of an embodiment of the balloon catheter-stent device according to the invention.

FIG. 3 shows, as a further embodiment, a folding protrusion 11, which in the end state shown here has the folding geometry of a simple tetrahedron, is again fixed to adjacent lattice bar elements 13a, 13b of a stent lattice structure, and forms a protrusion 14 protruding radially beyond the rest of the surface of the stent lattice structure.

Figure 4A:
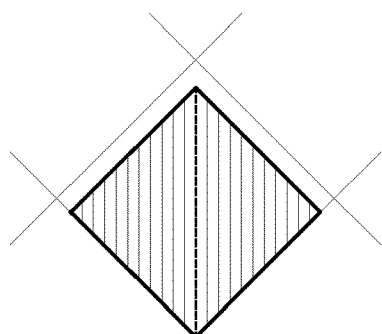
FIGS. 4A-4F show a schematic compilation of basic geometries of folding protrusion of balloon catheter-stent devices according to the invention, in each case in a plan view (left) and side view (right) in the dilated state of the stent.
Figure 4A:
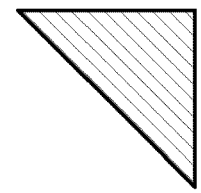
Figure 4B:
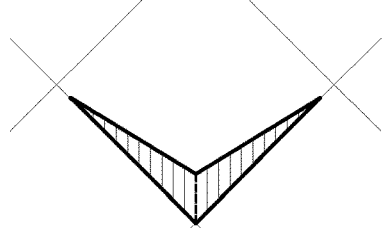
Figure 4B:
Figure 4C:
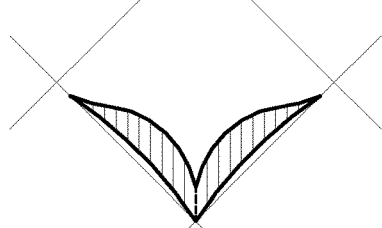
Figure 4C:
Figure 4D:
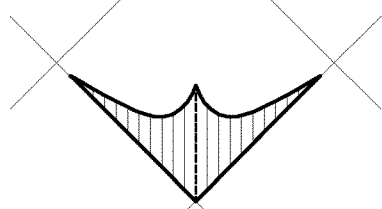
Figure 4D:
Figure 4E:
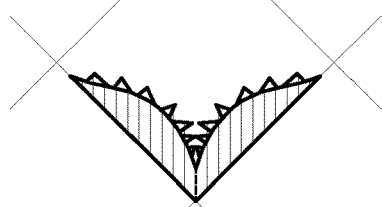
Figure 4E:
Figure 4F:
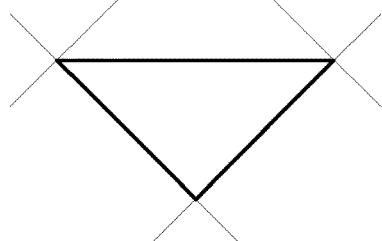
Figure 4F:
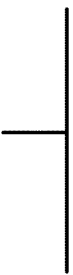

FIG. 4 shows sketches of further geometric configurations a) to f) of folding protrusions 10 and 14 in the erected end state, wherein protrusions (10 and 14) are formed with different angles (FIGS. 4A and 4B) or convexly curved edges (FIG. 4C) and concavely curved edges (FIG. 4D) or edges provided with a sawtooth geometry (FIG. 4E). FIG. 4F shows a folding protrusion geometry formed from individual bar elements.

Otherwise, the invention can also be embodied in a large number of modifications of the examples shown here and aspects of the invention described further above.

The invention claimed is:

1. A balloon catheter-stent device comprising:
   a balloon catheter comprising a catheter tube and a radially expandable balloon;
   a stent surrounding the balloon, the stent being radially expandable by inflation of the balloon;
   wherein the stent comprises at least one folding protrusion that is a plate-like structure and that unfolds with radial expansion and axial shortening of the stent to form an outer stent protrusion, and wherein the plate-like structure is directly attached along an entire length of each of two adjacent lattice bar elements of the stent, wherein the two adjacent lattice bar elements run in different directions and intersect each other.

2. The balloon catheter-stent device according to claim 1, wherein the at least one folding protrusion has a folded position with respect a global peripheral surface of the stent when folded and extends a height beyond the folded position when unfolded.

3. The balloon catheter-stent device according to claim 2, wherein the at least one folding protrusion is configured and connected to have an axial movement component and a radial and/or tangential movement component as it unfolds.

4. The balloon catheter-stent device according to claim 2, wherein the at least one folding protrusion in the folded position extends no more than 20% from a starting radius of a non-expanded state of the stent.

5. The balloon catheter-stent device according to claim 1, wherein the at least one folding protrusion has a substantially pyramid shape or superimposed tetrahedron shape when unfolded.

6. The balloon catheter-stent device according to claim 1, wherein the stent comprises a regular lattice structure formed of a repeating pattern of lattice bar elements and the at least one folding protrusion is formed at least partially by the two-adjacent lattice bar elements.

7. The balloon catheter-stent device according to claim 1, wherein end portions of the at least one folding protrusion comprise cross-sectional taperings or perforations as predetermined bending points.

8. The balloon catheter-stent device according to claim 1, wherein end portions of the at least one folding protrusion comprise a shape-memory material.

9. The balloon catheter-stent device according to claim 1, wherein the at least one folding protrusion comprises at least one cutting edge or sawing edge for engaging a stenosis in a cutting or sawing manner.

10. The balloon catheter-stent device according to claim 1, wherein the at least one folding protrusion is formed integrally with the rest of the structure of the stent.

11. The balloon catheter-stent device according to claim 1, wherein the at least one folding protrusion is formed from a different material than the stent.

12. The balloon catheter-stent device according to claim 1, wherein the stent and the at least one folding protrusion consist of a shape-memory material.

13. The balloon catheter-stent device according to claim 1, wherein the stent is connected to the balloon or the catheter tube.

14. The balloon catheter-stent device according to claim 1, wherein the at least one folding protrusion is attached to the surface of the stent in a planar manner and stretched between at least two stent struts or individual pieces of at least one stent strut having different directions.

15. A balloon catheter-stent device comprising:
a balloon catheter comprising a catheter tube and a radially expandable balloon;
a stent surrounding the balloon, the stent being radially expandable by inflation of the balloon;
wherein the stent comprises at least one folding protrusion that unfolds with radial expansion and axial shortening of the stent to form an outer stent protrusion, and wherein the at least one folding protrusion in the folded position extends between 1% and 10% from a starting radius of a non-expanded state of the stent.

16. A balloon catheter-stent device comprising:
a balloon catheter comprising a catheter tube and a radially expandable balloon;
a stent surrounding the balloon, the stent being radially expandable by inflation of the balloon;
wherein the stent comprises at least one folding protrusion that unfolds with radial expansion and axial shortening of the stent to form an outer stent protrusion, wherein the at least one folding protrusion is directly attached along an entire length of each of two adjacent lattice bar elements of the stent and wherein the at least one folding protrusion comprises at least one bent, convexly curved fixing edge for engagement in the wall of a blood vessel or organ.

17. A stent comprising a regular lattice structure formed of a plurality of lattice bar elements and at least one folding protrusion arranged within the lattice structure that is a plate-like structure and that unfolds with radial expansion and axial shortening of the stent to form an outer stent protrusion, wherein the at least one folding protrusion has a folded position with respect to a global peripheral surface of the stent when folded and extends a height beyond the folded position when unfolded, and wherein the plate-like structure is directly attached along an entire length of two adjacent ones of the plurality of lattice bar elements, wherein the two adjacent ones of the lattice bar elements run in different directions and intersect each other.

18. A balloon catheter-stent device comprising:
a balloon catheter comprising a catheter tube and a radially expandable balloon;
a stent surrounding the balloon, the stent being radially expandable by inflation of the balloon;
wherein the stent comprises at least one folding protrusion that is a plate-like structure and that unfolds with radial expansion and axial shortening of the stent to form an outer stent protrusion, wherein the at least one folding protrusion has a folded position with respect to a global peripheral surface of the stent when folded and extends a height beyond the folded position when unfolded, and wherein the at least one folding protrusion in the folded position extends between 1% and 10% from a starting radius of a non-expanded state of the stent.

* * * * *